(12) United States Patent
Comins et al.

(10) Patent No.: US 6,855,825 B2
(45) Date of Patent: Feb. 15, 2005

(54) SHORT SYNTHESIS OF PYRIDINE-BASED PHARMACEUTICAL INTERMEDIATES

(75) Inventors: Daniel L. Comins, Raleigh, NC (US); Shenlin Huang, Edison, NJ (US)

(73) Assignee: North Carolina State University, Raleigh, NC (US)

(*) Notice: Subject to any disclaimer, the term of this patent is extended or adjusted under 35 U.S.C. 154(b) by 22 days.

(21) Appl. No.: 10/739,256

(22) Filed: Dec. 18, 2003

(65) Prior Publication Data

US 2004/0138463 A1 Jul. 15, 2004

Related U.S. Application Data

(62) Division of application No. 10/320,329, filed on Dec. 16, 2002, now Pat. No. 6,706,884, which is a division of application No. 09/871,429, filed on May 31, 2001, now Pat. No. 6,534,656.

(51) Int. Cl.[7] .................. C07D 417/00; C07D 413/04; C07D 413/00; C07D 401/00
(52) U.S. Cl. ................ 546/268.7; 546/269.4; 546/271.1; 546/271.4; 546/272.4; 546/272.7
(58) Field of Search .......................... 546/268.7, 269.4, 546/271.1, 271.4, 272.1, 272.4, 272.7

(56) References Cited

FOREIGN PATENT DOCUMENTS

| WO | WO 01/21623 | 3/2001 |
| WO | WO 02/096878 | 12/2002 |

OTHER PUBLICATIONS

Cherng, Yie–Jia, *Synthesis of Substituted Pyridines by the Reactions of Halopyridines with Sulfur, Oxygen, and Carbon Nucleophiles under Focused Microwave Irradiation*, Tetrahedron, 58:4931–4935 (2002).

Fujimoto et al., *Substitution Reactions of Brominated Aromatic Heterocycles with Thiols*, Yakugaku Zasshi, 106(3):260–4 (1986).

Katrizky et al., *Reactivity of Six–Membered Rings: Alkyl Groups, Handbook of Heterocylic Chemistry*, pp. 256–257 ($2^{nd}$ Ed., 2000).

*Primary Examiner*—Cecilia J. Tseng
*Assistant Examiner*—Binta Robinson
(74) *Attorney, Agent, or Firm*—Myers Bigel Sibley & Sajovec

(57) ABSTRACT

A method of making a compound of Formula VI:

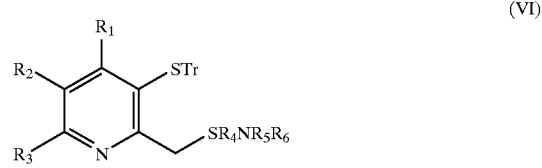

wherein Tr is a triphenyl group; $R_1$, $R_2$ and $R_3$ are each independently selected from the group consisting of H, C1–C4 alkyl, C1–C4 alkoxy, aryl, heteroaryl, and arylalkyl; $R_4$ is C2–C6 alkyl, and $R_5$ and $R_6$ are each independently H or C1–C4 alkyl, involves the step of reacting a compound of Formula V:

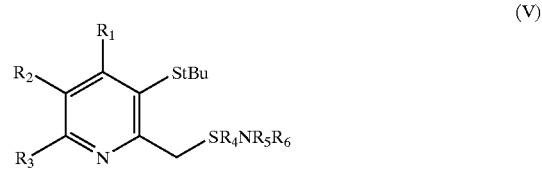

with Tr-OH to produce a compound of Formula VI. The compounds of Formula VI are useful as intermediates in the manufacture of antibiotic agents. Methods of making compounds of Formula V, and intermediates made or used in the foregoing methods, are also described.

6 Claims, No Drawings

SHORT SYNTHESIS OF PYRIDINE-BASED PHARMACEUTICAL INTERMEDIATES

RELATED APPLICATIONS

This application is a divisional of U.S. application Ser. No. 10/320,329, filed Dec. 16, 2002, now issued as U.S. Pat. No. 6,706,884, which in turn is a divisional of U.S. application Ser. No. 09/871,429, filed May 31, 2001, now issued as U.S. Pat. No. 6,534,656, the disclosures of both of which are hereby incorporated herein in their entirety by reference.

FIELD OF THE INVENTION

The present invention concerns methods for the synthesis of pyridine-based compounds, which compounds are useful as intermediates for the manufacture of pharmaceutical compounds.

BACKGROUND OF THE INVENTION

Over the past three decades a large variety of antibiotics have become available for clinical use. Unfortunately, the wide-spread use of these antibiotics has caused a rapid increase in the number of bacterial strains that are resistant to the currently available antibiotics.

S. Hecker et al., PCT Application WO 01/21623 (published 29 Mar. 2001), describes 7-acylamino-3-heteroarylthio-3-cephem carboxylic acid antibiotics and prodrugs thereof. The compounds described therein are active as antibiotics against a wide spectrum of organisms including organisms which are resistant to beta-lactam antibiotics. However, the compounds described therein are complicated, and require the synthesis of a variety of separate groups. One group which must be synthesized to make these compounds is the C3 side-chain, an intermediate for which is illustrated on page 51 therein as follows:

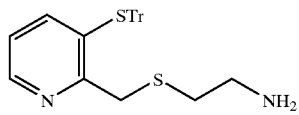

However, the synthesis of such C3 side chain groups as set forth in S. Hecker et al. requires in excess of 6 steps (see pages 49–52 therein). Accordingly, there is a need for new ways to make the intermediates used to make the antibiotic compounds described in S. Hecker et al.

SUMMARY OF THE INVENTION

Accordingly, a first aspect of the present invention is a method of making a compound of Formula VI:

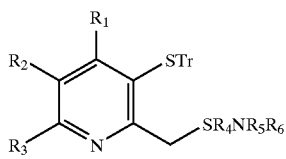

(VI)

wherein:
Tr is a triphenyl group;
$R_1$, $R_2$ and $R_3$ are each independently selected from the group consisting of H, C1–C4 alkyl, C1–C4 alkoxy, aryl, heteroaryl, and arylalkyl;
$R_4$ is C2–C6 alkyl, and
$R_5$ and $R_6$ are each independently H or C1–C4 alkyl, comprising:
reacting a compound of Formula V:

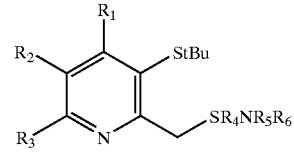

(V)

with Tr-OH to produce a compound of Formula VI.

A second aspect of the present invention is a method of making a compound of Formula V as described above, the method comprising reacting a compound of Formula IV:

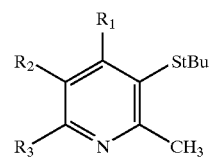

(IV)

where tBu is tert-Butyl or other suitable leaving group, with $R_6R_5NR_4SSR_4NR_5R_6$ in the presence of a strong amide base to produce a compound of Formula V.

A third aspect of the present invention is a method of a compound of Formula IV as described above, comprising reacting a compound of Formula III:

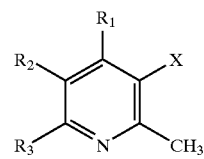

(III)

wherein X is halogen, with sodium tert-butylthiolate or potassium tert-butylthiolate to produce a compound of Formula IV.

A fourth aspect of the present invention is a compound of Formula VI:

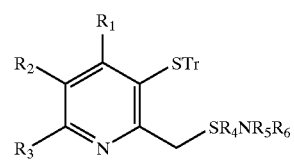

(VI)

wherein:
Tr is a triphenyl group;
$R_1$, $R_2$ and $R_3$ are each independently selected from the group consisting of H, C1–C4 alkyl, C1–C4 alkoxy, aryl, heteroaryl, and arylalkyl;
$R_4$ is C2–C6 alkyl, and
$R_5$ and $R_6$ are each independently H or C1–C4 alkyl;
subject to the proviso that (i) $R_1$, $R_2$ and $R_3$ are not all simultaneously H, or (ii) $R_4$ is not C2, or (iii) $R_5$ and $R_6$ are not simultaneously H.

A further aspect of the present invention is a compound of Formula V:

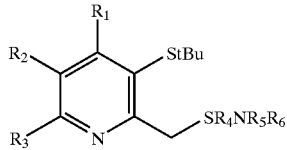

(V)

wherein:
tBu is tert-butyl, or other suitable leaving group;
$R_1$, $R_2$ and $R_3$ are each independently selected from the group consisting of H, C1–C4 alkyl, C1–C4 alkoxy, aryl, heteroaryl, and arylalkyl;
$R_4$ is C2–C6 alkyl, and
$R_5$ and $R_6$ are each independently H or C1–C4 alkyl.

Compounds of Formula VI above are useful as intermediates in the manufacture of antibiotic compounds.

Compounds of Formula V above are useful as intermediates in the manufacture of compounds of Formula VI.

The foregoing and other objects and aspects of the present invention are explained in greater detail in the specification set forth below.

DETAILED DESCRIPTION OF PREFERRED EMBODIMENTS

"Alkyl" as used herein refers to linear or branched alkyl, preferably linear alkyl, including but not limited to methyl, ethyl, propyl, and butyl (Bu).

"Halo" as used herein refers to any suitable halogen group, such as fluoro, chloro) bromo, or iodo.

"Aryl" as used herein refers to any suitable aromatic group, such as phenyl, which aromatic group may be substituted or unsubstituted.

"Arylalkyl" as used herein refers to any suitable aryl group covalently coupled to an alkyl group, such as benzyl.

"Triphenyl" or "Tr" groups as used herein may be unsubstituted or substituted one or more times by additional groups such as C1–C4 alkyl, C1–C4 alkyloxy, or halo. Para substitutions are preferred, but substitutions may be of any number from 1 to 5 and in any position, with mono or di substitutions preferred.

As noted above, a first aspect of the present invention is a method of making a compound of Formula VI:

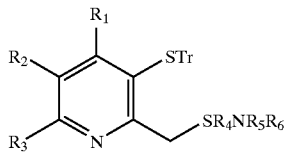

(VI)

wherein:
Tr is a triphenyl group;
$R_1$, $R_2$ and $R_3$ are each independently H C1–C4 alkyl, C1–C4 alkoxy, aryl, heteroaryl, or arylalkyl (preferably H),
$R_4$ is C2–C6 alkyl (preferably C2), and
R5 and $R_6$ are each independently H or C1–C4 alkyl (preferably H).

The method comprises reacting a compound of Formula V:

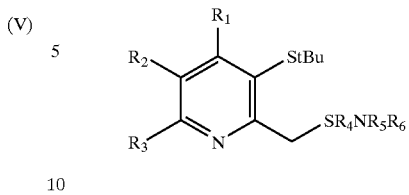

(V)

with Tr-OH to produce a compound of Formula VI. The reacting step is may be carried out as a one-pot, two step reacting step. The reaction step is preferably carried out in the presence of a strong organic acid, examples including but not limited to methanesulfonic acid and arylsulfonic acid (e.g., paratoluene sulfonic acid). The reacting step is typically carried out in a polar solvent such as acetic acid, which solvent is preferably non-aqueous, and may be carried out at any suitable temperature such as at room temperature.

Compounds of Formula VI are useful, among other things, as C-3 side chain intermediates useful for the production of 7-acylamino-3-heterarylthio-3-cephem carboxylic acid antibiotics, and prodrugs thereof, as shown in S. Hecker et al., PCT Application WO 01/21623 (29 Mar. 2001) (see pages 49–50). Particularly organisms for which the compounds of the invention may be used as antibiotics include but are not limited to *Staphylococcus aureus*, *Enterobacteriaceae*, and *Pseudomonas*. The compounds may be used in vivo as a pharmaceutical agent by (for example), oral, parenteral, or topical administration, or may be used in vitro, for example as a topical or surface antibiotic.

A compound of Formula V above may be produced by reacting a compound of Formula IV:

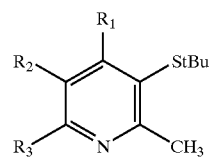

(IV)

with $R_6R_5NR_4SSR_4NR_5R_6$ (which may be produced in accordance with known techniques), preferably in the presence of a strong amide base, to produce a compound of Formula V. This reacting step may be carried out in any suitable solvent, typically an etherial solvent such as dialkyl ether (e.g., diethyl ether), dimethoxyethane, tetrahydrofuran, or mixtures thereof. Any suitable strong amide base may be used, such as lithium, sodium, and potassium amide bases. Any suitable amide may be used, such as a dialkyl amide (e.g., diethyl amide). The temperature at which the reacting step is carried out is not critical, but is preferably less than room temperature (e.g., from −80 to −20 or even 0 degrees centigrade).

The compound of Formula IV above may be produced by reacting a compound of Formula III:

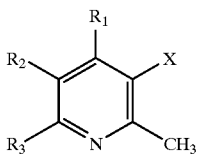

(III)

wherein X is halogen, with sodium tert-butylthiolate or potassium tert-buthylthiolate to produce a compound of Formula IV. This reacting step may be carried out in any suitable solvent, preferably nonaqueous, such as a polar aprotic solvent (e.g., dimethylformamide and/or dimethylsulfoxide). The reacting step may be carried out at any suitable temperature, such as from 20 to 120 or 130 degrees centigrade. Compounds of Formula III are known or may be prepared in accordance with known techniques.

The present invention is explained in greater detail in the following non-limiting examples.

EXAMPLES 1–4

Examples 1 to 4 below illustrate the set of reactions shown in Scheme 2 below.

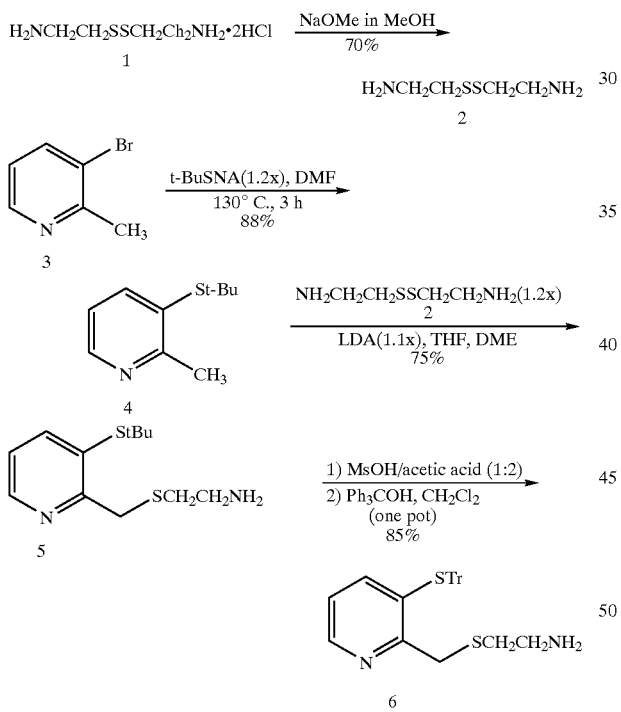

Example 1

Cystamine (2)

To a suspension of cystamine dihydrochloride (1) (10.0 g, 44.4 mmol) in anhydrous methanol (20 mL) was added NaOMe (20 mL, 88.8 mmol, 25 wt. % solution in methanol) slowly. The mixture was stirred for 0.5 h and then filtered through a fritted funnel. The solvent was removed in vacuo without heating (caution: heating the solution can cause decomposition of cystamine). The residue was dissolved in diethyl ether and then filtered. The filtrate was concentrated in vacuo and the residue was bulb-to-bulb distilled (120° C., 0.5 mmHg) to afford 4.8 g (70%) of the desired product 2 as a colorless liquid. The oil was dissolved in DME and used directly in the next step.

Example 2

3-tert-Butylsulfanyl-2-methylpyridine (4)

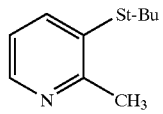

To a solution of 3-bromo-2-methyl-pyridine (3) (15.0 g, 87.1 mmol) in DMF (100 mL) was added sodium tert-butylthiolate (11.7 g, 104.5 mmol) under $N_2$. The mixture was heated to 130° C. for 3 h. After cooling, it was poured into EtOAc (200 mL) and washed with water (3×100 mL). The organic layer was dried over $MgSO_4$ and the solvent was removed in vacuo. The residue was bulb-to-bulb distilled (90° C., 0.5 mmHg) to afford 13.9 g (88%) of the desired product as a colorless liquid. FTIR (thin film) 2962, 1559, 1419, 1364, 1168 cm$^{-1}$. $^1$H NMR (300 MHz, CDCl$_3$) δ 1.30 (s, 9H), 2.77 (s, 3H), 7.10 (t, J=4.7 Hz, 1H), 7.79 (d, J=7.7 Hz, 1H), 8.47 (d, J=4.4 Hz, 1H). $^{13}$C NMR (75 MHz, CDCl$_3$) δ 24.3, 30.8 (isomer), 31.0, 47.7, 120.9, 123.0 (isomer), 128.5, 144.7 (isomer), 146.0, 149.0, 156.3 (isomer), 163.7. HRMS calcd. for $C_{10}H_{16}NS$ (M+H)$^+$: 182.1003. Found: 182.1006 (M+H)$^+$.

Example 3

2-[(3-tert-Butylsulfanyl)pyridin-2-ylmethylsulfanyl] ethylamine (5)

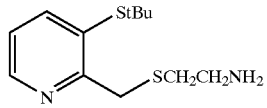

To a three-necked flask equipped with a mechanical stirrer was added THF (200 mL), n-BuLi (17.4 mL, 43.5 mmol, 2.5 M in hexane) and isopropylamine (5.7 mL, 43.5 mmol) at −78 ° C. After 30 minutes, compound 4 (7.1 g in 20 mL THF, 39.5 mmol) was added dropwise. After stirring for 15 minutes, cystamine (2) (7.2 g in 20 mL DME, 47.3 mmol) was added in one portion. The mixture was warmed to rt slowly and stirred overnight. It was poured into water (100 mL) and extracted with EtOAc (3×100 mL). The combined organic layers were dried over $MgSO_4$, and the solvent was removed in vacuo. The residue was bulb-to-bulb distilled (150° C., 0.5 mmHg) to afford 7.5 g (75%) of the desired product as a brown liquid. FTIR (thin film) 3357, 2961, 1560, 1458, 1364 cm$^{-1}$. $^1$H NMR (300 MHz, CDCl$_3$) δ 1.31 (s, 9H), 2.66 (t, J=6.2 Hz, 2H), 2.88 (t, J=6.2 Hz, 2H), 4.20 (s, 2H), 7.16 (dd, J=7.7, 4.7 Hz, 1H), 7.83 (d, J=7.8 Hz, 1H), 8.53 (d, J=4.6 Hz, 1H). $^{13}$C NMR (75 MHz, CDCl$_3$) δ 31.2, 36.2, 36.3, 41.3, 47.9, 121.9, 128.6, 146.1, 149.3, 163.6. HRMS calcd. for $C_{12}H_{21}N_2S_2$ (M+H)$^+$: 257.1146. Found: 257.1143 (M+H)$^+$.

Example 4

2-[3-(Triphenylsulfanyl)pyridin-2-ylmethylsulfanyl]ethylamine (6)

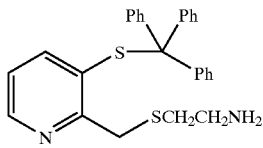

To an argon purged flask was added compound 5 (0.36 g, 1.40 mmol), methanesulfonic acid (2 mL) and acetic acid (4 mL). The mixture was heated to reflux for 20 h and then the solvent was removed in vacuo. The residue was dissolved in dichloromethame (20 mL) and triphenylmethanol (0.44 g, 1.68 mmol) was added. After stirring at rt for 1 h, the mixture was poured into aqueous $NaHCO_3$ with caution and then extracted with dichloromethane (2×50 mL). The combined organic layers were dried over $MgSO_4$ and the solvent was removed in vacuo. The residue was purified by radial PLC (methanol) to afford 0.52 g (85%) of the desired product as a thick white oil. FTIR (thin film) 3363, 3055, 1599, 1489 $cm^{-1}$. $^1$H NMR (300 MHz, $CDCl_3$) δ 1.93 (br s, 2H), 2.51 (m, 2H), 2.75 (m, 2H), 3.48 (s, 2H), 6.70 (m, 1H), 7.12–7.37 (m, 16H), 8.19 (d, J=4.1 Hz, 1H). $^{13}$C NMR (75 MHz, $CDCl_3$) δ 31.1, 35.5, 41.0, 71.6, 121.4, 126.9, 127.0, 127.2, 127.8, 129.8, 130.7, 141.6, 143.6, 147.4, 161.5. HRMS calcd. for $C_{27}H_{26}N_2S_2$: 443.1616 $(M+H)^+$. Found: 443.1618 $(M+H)^+$.

The foregoing is illustrative of the present invention, and is not to be construed as limiting thereof. The invention is defined by the following claims, with equivalents of the claims to be included therein.

What is claimed is:

1. A method making a compound of Formula IV:

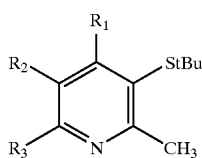

(IV)

wherein:

tBu is tert-butyl; and $R_1$, $R_2$ and $R_3$ are each independently selected from the group consisting of H, C1–C4 alkyl, C1–C4 alkoxy, aryl, heteroaryl, and arylalkyl; comprising:

reacting a compound of Formula III:

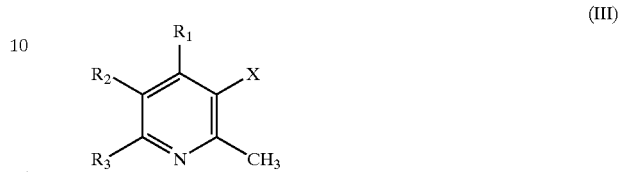

(III)

wherein X is halogen, with sodium tert-butylthiolate or potassium tert-buthylthiolate to produce a compound of Formula IV.

2. A method according to claim 1, wherein said reacting step is carried out in a polar aprotic solvent.

3. A method according to claim 1, wherein said reacting step is carried out in a nonaqueous solvent.

4. A method according to claim 1, wherein said reacting step is carried out in a solvent selected from the group consisting of dimethylformamide and dimethylsulfoxide.

5. A method according to claim 1, wherein said reacting step is carried out at a temperature of from 20 to 130 degrees centigrade.

6. A compound of Formula IV:

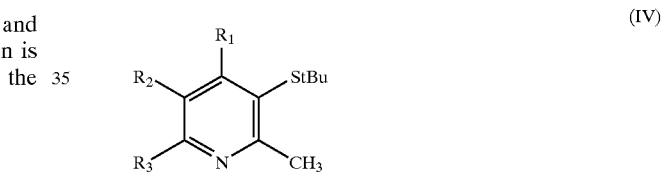

(IV)

wherein:

tBu is tert-butyl; and $R_1$, $R_2$, and $R_3$ are each independently selected from the group consisting of H, C1–C4 alkyl, C1–C4 alkoxy, aryl, heteroaryl, and arylalkyl.

* * * * *